United States Patent [19]

Junek et al.

[11] Patent Number: 4,950,754
[45] Date of Patent: Aug. 21, 1990

[54] CHROMOGENIC DICYANOMETHYLENEPYRAZOLINONES

[75] Inventors: Hans Junek; Manfred Klade, both of Graz, Austria

[73] Assignee: Ciba-Geigy Corporation, Ardsley, N.Y.

[21] Appl. No.: 467,623

[22] Filed: Jan. 19, 1990

Related U.S. Application Data

[62] Division of Ser. No. 363,650, Jun. 8, 1989, Pat. No. 4,916,234.

[30] Foreign Application Priority Data

Jun. 17, 1988 [CH] Switzerland ............... 2355/88

[51] Int. Cl.$^5$ ............... C07D 401/04; C07D 417/14
[52] U.S. Cl. ............... 544/58.5; 544/58.6; 544/58.7; 544/131; 544/139; 544/140; 544/364; 544/370; 544/371; 546/194; 546/210; 546/211; 546/279; 548/336; 548/364
[58] Field of Search ............... 544/58.5, 58.6, 58.7, 544/131, 139, 140, 364, 370, 371; 546/194, 210, 211, 279; 548/336, 364

[56] References Cited

U.S. PATENT DOCUMENTS 2,165,445  7/1939  Boese, Jr. ............... 548/364

*Primary Examiner*—Robert W. Ramsuer
*Attorney, Agent, or Firm*—Kevin T. Mansfield; Edward McC. Roberts

[57] ABSTRACT

Chromogenic dicyanomethylenepyrazolinone for thermographic recording processes and the corresponding cyanomethylene dyes of the formula

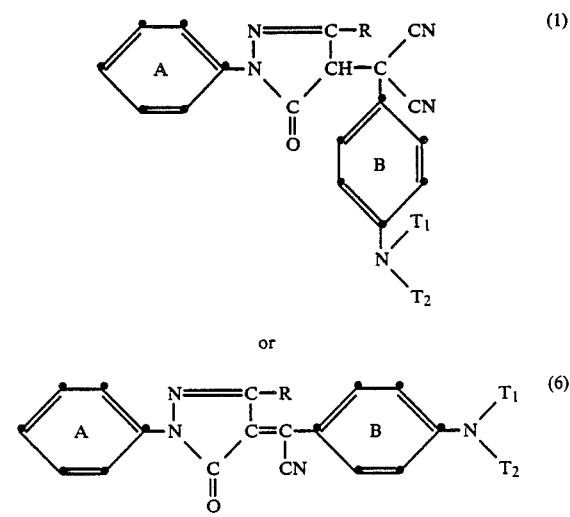

in which R is hydrogen, hydroxyl, amino, alkyl, cycloalkyl, aryl, aralkyl or a heterocylic radical, $T_1$ and $T_2$, independently of one another, are each hydrogen, unsubstituted or halogen-, hydroxyl-, cyano- or lower alkoxy-substituted alkyl having a maximum of 12 carbon atoms, cycloalkyl having 5 to 10 carbon atoms or unsubstituted or halogen-, cyano-, lower alkyl- or lower alkoxy-(ring)substituted phenalkyl or phenyl, or $T_1$ and $T_2$ together with the nitrogen linking them are a five- or six-membered heterocyclic radical, and rings A and B, independently of one another, are unsubstituted or substituted by halogen, cyano, nitro, lower alkyl, lower alkoxy, (lower alkyl)carbonyl or (lower alkoxy)carbonyl.

5 Claims, No Drawings

CHROMOGENIC DICYANOMETHYLENEPYRAZOLINONES

This is a divisional of application Ser. No. 363,650 filed on Jun. 8, 1989, now U.S. Pat. No. 4,916,234.

The present invention relates to chromogenic dicyanomethylene-pyrazolinones and the corresponding cyanomethylene dyes and processes for their preparation and their use.

The chromogenic dicyanomethylenepyrazolinones according to the invention have the general formula

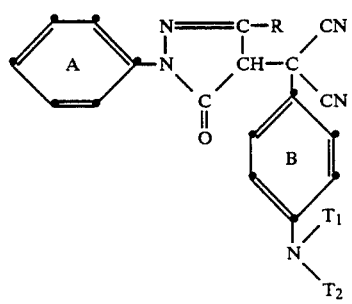

in which R is hydrogen, hydroxyl, amino, alkyl, cycloalkyl, aryl, aralkyl or a heterocylic radical, $T_1$ and $T_2$, independently of one another, are each hydrogen, unsubstituted or halogen-, hydroxyl-, cyano- or lower alkoxy-substituted alkyl having a maximum of 12 carbon atoms, cycloalkyl having 5 to 10 carbon atoms or unsubstituted or halogen-, cyano-, lower alkyl- or lower alkoxy-(ring) substituted phenalkyl or phenyl, or $T_1$ and $T_2$ together with the nitrogen linking them are a five- or six-membered, preferably saturated, heterocyclic radical, and rings A and B, independently of one another, are unsubstituted or substituted by halogen, cyano, nitro, lower alkyl, lower alkoxy, (lower alkyl)carbonyl or (lower alkoxy)carbonyl.

In the definition of the radicals of the pyrazolinones, lower alkyl and lower alkoxy are those groups or parts of groups which have 1 to 5, in particular 1 to 3, carbon atoms, for example methyl, ethyl, n-propyl, isopropyl, n-butyl, sec.-butyl, tert.-butyl or amyl or methoxy, ethoxy, isopropoxy, tert.-butoxy or tert. amyloxy.

For example, halogen is fluorine, bromine or, preferably, chlorine. Alkyl groups R, $T_1$ and $T_2$ can have 1 to 12 C atoms and be straight-chain or branched. Examples of these alkyl radicals are methyl, ethyl, n-propyl, isopropyl, n-butyl, sec.-butyl, amyl, n-hexane, 2-ethylhexyl, n-heptyl, n-octyl, isooctyl, n-nonyl, isononyl or n-dodecyl.

Substituted alkyl radicals in $T_1$ and $T_2$ can be in particular cyanoalkyl, halogenoalkyl, hydroxyalkyl or alkoxyalkyl each having preferably a total of 2 to 6 carbon atoms, for example β-cyanoethyl, β-chloroethyl, γ-chloropropyl, β-hydroxyethyl, γ-hydroxypropyl, β-methoxyethyl or β-ethoxyethyl.

Examples of $T_1$ and $T_2$ as cycloalkyl are cyclopentyl or preferably cyclohexyl.

R, $T_1$ and $T_2$ as aralkyl are usually phenylethyl, phenylisopropyl or in particular benzyl, while R, $T_1$ and $T_2$ as aryl are advantageously naphthyl, diphenyl and in particular phenyl. The benzyl and phenyl radicals can be substituted by halogen, trifluoromethyl, cyano, nitro, lower alkyl, lower alkoxy, (lower alkoxy)carbonyl or (lower alkyl)carbonyl.

Preferred substituents in the benzyl and phenyl group of the R and T radicals are, for example, halogen, cyano, methyl, methoxy or carbomethoxy. Examples of this type of araliphatic or aromatic radicals are methylbenzyl, 2,4- or 2,5-dimethylbenzyl, chlorobenzyl, dichlorobenzyl, cyanophenyl, tolyl, xylyl, chlorophenyl, methoxyphenyl or carbomethyoxyphenyl.

A heterocyclic radical R is in particular a 5- or 6-membered, preferably oxygen-, sulfur- or nitrogen-containing heterocycle of aromatic character. Examples of these heterocycles are thienyl, furyl, furfuryl, pyrrolyl, pyrazolyl, imidazolyl or pyridyl radicals. The heteroaromatic radicals are advantageously bound to the pyrazolinone ring via a carbon atom of the hetero ring.

Where $T_1$ and $T_2$ together with the common nitrogen atom are a heterocyclic radical, this radical is, for example, pyrrolidino, piperidino, pipecolino, morpholino, thiomorpholino or piperazino, for example methylpiperazino. Preferred saturated heterocyclic radicals for $-NT_1T_2$ pyrrolidino, piperidino or morpholino.

The substituent R is preferably lower alkyl, for example methyl, ethyl, propyl, or also amino, hydroxyl or phenyl.

$T_1$ and $T_2$ can be identical to or different from one another. $T_1$ is preferably $C_1-C_8$alkyl, cyclohexyl, phenyl, tolyl, benzyl or in particular lower alkyl such as methyl, ethyl or butyl. $T_2$ is preferably hydrogen, lower alkyl or benzyl and especially methyl, ethyl or butyl.

Benzene rings A and B are preferably unsubstituted. However, they can have 1 to 4 (preferably 1 to 2) substituents. Preferred substituents are halogen, nitro, lower alkyl (in particular methyl) or lower alkoxy, for example methoxy.

Particularly important dicyanomethylenepyrazolinones have the formula

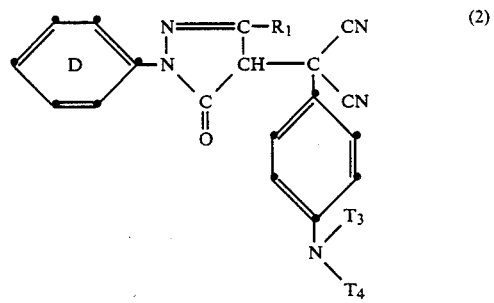

in which $R_1$ is amino, hydroxyl, lower alkyl, cyclohexyl or phenyl, and $T_3$ is lower alkyl, cyclohexyl, phenyl, tolyl or benzyl, and $T_4$ is hydrogen, lower alkyl or benzyl, and ring D is unsubstituted or substituted by halogen, nitro, lower alkyl or lower alkoxy.

Of the dicyanomethylenepyrazolinones of the formula (2), those in which $R_1$ is amino or lower alkyl, $T_3$ is lower alkyl and $T_4$ is hydrogen or lower alkyl and benzene ring D is unsubstituted or substituted by methyl or halogen are preferred.

The dicyanomethylenepyrazolinones of the formula (1) and (2) are 4'-aminophenyl-4-(1-phenyl-2-pyrazolin-5-one)malodinitrile compounds. They are prepared by adding an aromatic amine of the formula

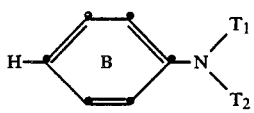

in which B, $T_1$ and $T_2$ are as defined above onto a dicyanomethylenepyrazolinone compound of the formula

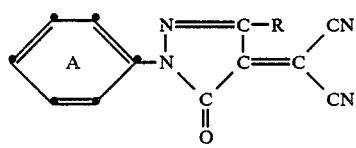

in which A and R are as defined above.

The addition reaction is advantageously carried out in protic solvents at a temperature of 20° to 60° C., preferably 30° to 50° C. Suitable solvents of this type are lower alkanols, for example methanol, ethanol, isopropanol or butanol, ketones, for example acetone, methyl isopropyl ketone or diethyl ketone and acetonitrile, propionitrile, dimethylformamide and especially glacial acetic acid.

Suitable aromatic amines are in particular N-monoalkyl- or N,N-dialkylanilines, for example N-methylaniline, N-ethylaniline, N-isopropylaniline, N,N-dimethylaniline, N,N-diethylaniline, N,N-dibutylaniline and also N,N-dibenzylaniline, N-phenylaniline and N-phenylpyrrolidines.

The dicyanomethylenepyrazolinone compounds of the formula (4) which can be used as starting materials are in particular 4-dicyanomethylene-3-methyl-1-phenyl-2-pyrazolin-5-one, m.p. 178° C., 4-dicyanomethylene-3-methyl-1-p-tolyl-2-pyrazolin-5-one, m.p. 145° C., 4-dicyanomethylene-3-propyl-1-phenyl-2-pyrazolin-5-one, m.p. 110°–112° C., 4-dicyanomethylene-1,3-diphenyl-2-pyrazolin-5-one, m.p. 162° C. and 4-dicyanomethylene-3-amino-1-phenyl-2-pyrazolin-5-one, m.p. 220° C. (dec.).

The starting materials of the formula (4) are novel. In general it can be said that it is possible to obtain them, for example, by reaction of a pyrazolinone compound of the formula

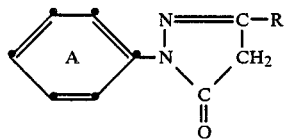

in which A and R are as defined above with tetracyanoethylene, advantageously in the presence of an inert organic solvent, for example acetonitrile, propionitrile or lower alkanols, particularly ethanol or isopropanol, and at a temperature of 20° to 50° C.

The compounds of the formulae (1) and (2) according to the invention can be used as colour formers in a thermoreactive recording material.

The hue of the printed image obtained in the heat-sensitive recording material can be red, violet or reddish blue, depending on the definition of A and R, and the colour images are sharp and clear.

The heat-sensitive recording materials are used, for example, for recording information, for example in electronic calculators, teleprinters, telex machines or in recording machines and measuring instruments, for example electrocardiographs. The image formation (marking) can also take place manually by means of a heated pen. A further means of producing markings by means of heat are laser beams.

The heat-sensitive recording systems contain at least one substrate, for example paper, synthetic paper or a plastic sheet and on top of it one or more heat-sensitive layers containing the dicyanomethylenepyrazolinone compounds of the formulae (1) and (2).

Preferably, the thermoreactive recording material is prepared by using meltable, film-forming binders. These binders are usually water-soluble, while the dicyanomethylene-pyrazolinone compounds of the formulae (1) and (2) are insoluble in water. The binder should be capable of dispersing and fixing the dicyanomethylenepyrazolinone compound at room temperature.

Upon exposure to heat, a proton and a cyanide ion are removed from the dicyanomethylene compound which acts as colour former and a colour is formed.

Water-soluble or at least water-swellable binders are, for example, hydrophilic polymers such as polyvinyl alcohol, polyacrylic acid, hydroxyethylcellulose, methylcellulose, carboxymethylcellulose, polyacrylamide, polyvinylpyrrolidone, carboxylated butadiene/styrene copolymers, gelatin, starch or etherified corn starch.

The thermoreactive layers can contain further additives. To improve the whiteness, to facilitate the printing of the papers and to prevent the heated pen from being glued on, these layers can contain, for example, talcum, titanium dioxide, zinc oxide, alumina, aluminium hydroxide, calcium carbonate (e.g. chalk), clays or also organic pigments, for example urea/formaldehyde polymers. To make sure that the colour is only formed within a limited temperature range, substances such as urea, thiourea, diphenylthiourea, acetamide, acetanilide, benzenesulfanilide, stearamide, phthalic anhydride, metal stearates, for example zinc stearate, phthalonitrile, dimethyl terephthalate or other suitable meltable products which induce CN elimination can be added. Preferably, the thermographic recording materials contain waxes, for example carnauba wax, montan wax, paraffin wax, polyethylene wax, condensation products of higher fatty acid amides and formaldehydes and condensation products of higher fatty acids and ethylenediamine. If desired, the recording materials can also contain alkylene substances, for example hydroxides or carbonates of alkali metals or, preferably open-chain or cyclic organic bases such as amines, alkanolamines, guanidines, pyridines or imidazole derivatives.

Upon exposure to heat, HCN is eliminated from the dicyanomethylenepyrazolinones of the formula (1) to give monocyanomethylenepyrazolinones of the formula

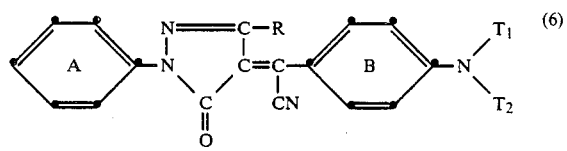

in which A, B, R, $T_1$ and $T_2$ are as defined above.

The compounds of the formula (6) are coloured products and can have various uses as dyes.

The preparative thermolysis is advantageously carried out by heating to temperatures of more than 70° C., preferably to temperatures of 80° to 120° C. It is advantageously carried out in the presence of an inert organic solvent, for example glacial acetic acid or dimethylformamide, and under reflux. If desired, it is also possible to add an alkali metal compound, for example alkali metal carbonates or alkali metal bicarbonates, ammonium carbonate or ammonium bicarbonate.

The elimination of cyanide for preparing the dyes of the formula (6) can also be carried out by photolysis, advantageously by irradiation, for example with ultraviolet light and, especially, by means of a mercury low-pressure lamp, in methanolic solution. In this case, it is not necessary to isolate the dicyanomethylenepyrazolinones of the formula (1) during their preparation.

In the examples which follow, the percentages and parts given are by weight.

EXAMPLE 1

(a) 1.28 g of tetracyanoethylene are dissolved in 20 ml of acetonitrile, warmed to 40° C., and 0.87 g of 3-methyl-1-phenyl-2-pyrazolin-5-one is slowly added with stirring. The mixture is cooled, filtered off, and water is added to the filtrate. The resulting precipitate is filtered off and recrystallized from ethanol. This gives 1 g of the compound of the formula

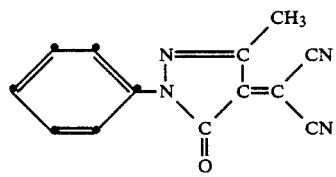

(i)

m.p. 178° C.

(b) 8.5 mmol of 4-dicyanomethylene-3-methyl-1-phenyl-2-pyrazolin-5-one of the formula (i) are stirred together with 16.0 mmol of N,N-dimethylaniline in 30 ml of glacial acetic acid at room temperature, which rapidly leads to the formation of a precipitate. Stirring at 30°–50° C. is continued for another 2 hours, the precipitate is filtered off and washed with ethanol. The compound is analytically pure. This gives a colourless compound of the formula

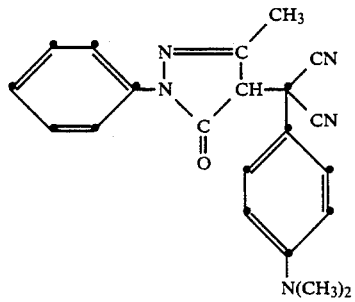

(11)

Yield 86% of theory. m.p. 160° C.

A solution of this compound in methanol has a $\lambda_{max}$ at 276 nm.

EXAMPLE 2

(a) 1.75 g of 3-amino-1-phenyl-2-pyrazolin-5-one are stirred with 1.28 g of tetracyanoethylene in 60 ml of ethanol at room temperature for 30 minutes. 2.2 g of the resulting precipitate are then recrystallized from butanol. This gives a compound of the formula

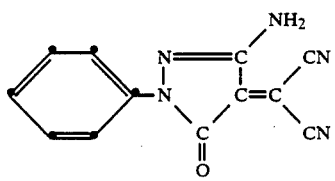

(ii)

m.p. 220° C. (dec.)

(b) 8.5 mmol of 3-amino-4-dicyanomethylene-1-phenyl-2-pyrazolin-5-one of the formula (ii) are stirred together with 16.0 mmol of N,N-dimethylaniline in 30 ml of glacial acetic acid at room temperature, which rapidly leads to decolourization and formation of a precipitate. Stirring at 30°–50° C. is continued for another 2 hours, the precipitate is filtered off and washed with ethyl acetate. The compound is analytically pure. This gives a colourless compound of the formula

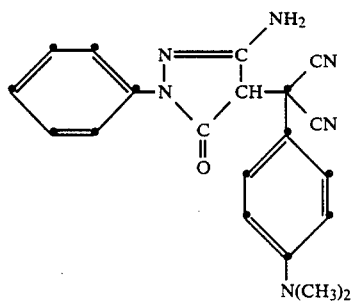

(12)

Yield 80% of theory. m.p. 162° C.

A solution of this compound in methanol has a $\lambda_{max}$ at 275 nm.

The procedure described in Examples 1 and 2 is repeated, using the corresponding reactants, to give the dicyanomethylenepyrazolinones listed in Table 1 below.

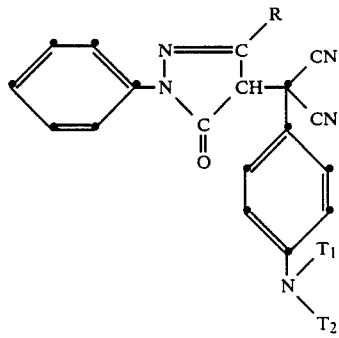

(13)

TABLE 1

| Ex. | R | —NT$_1$T$_2$ | m.p./°C. | Yield in % | $\lambda_{max}$ (nm) in methanol |
|---|---|---|---|---|---|
| 3 | CH$_3$ | —N(C$_2$H$_5$)$_2$ | 180 | 99 | 262 |
| 4 | CH$_3$ | —NHC$_2$H$_5$ | 178 | 89 | 270 |
| 5 | NH$_2$ | —N(C$_2$H$_5$)$_2$ | 188 | 92 | 270 |
| 6 | NH$_2$ | —NHC$_2$H$_5$ | 170 | 86 | 270 |

EXAMPLE 7

3 mmol of the compound of the formula (11) according to Example 1(b) are heated to reflux in 10 ml of dimethylformamide for 30 to 90 minutes. The mixture is cooled and water is added with stirring, which precipitates the compound of the formula

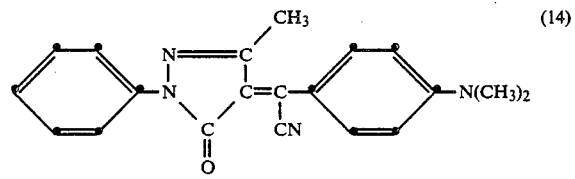
(14)

in the form of green-black crystals. The compound is recrystallized from xylene or toluene. Melting point 169° C. (dec.), yield 82% of theory.

A solution of this compound in methanol has a $\lambda_{max}$ at 545 nm.

The procedure described in Example 7 is repeated, using the compounds according to Examples 2 to 6, to give the cyanomethylenepyrazolinones of the formula (15) listed in Table 2.

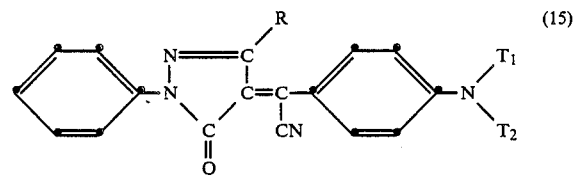
(15)

TABLE 2

| Ex. | R | —NT$_1$T$_2$ | m.p./°C. | Yield in % | $\lambda_{max}$ (nm) in methanol |
|---|---|---|---|---|---|
| 8 | CH$_3$ | —N(C$_2$H$_5$)$_2$ | 133 dec. | 90 | 560 |
| 9 | CH$_3$ | —NHC$_2$H$_5$ | 203 dec. | 86 | 540 |
| 10 | NH$_2$ | —N(CH$_3$)$_2$ | 182 dec. | 68 | 525 |
| 11 | NH$_2$ | —N(C$_2$H$_5$)$_2$ | 188 dec. | 70 | 535 |
| 12 | NH$_2$ | —NH—C$_2$H$_5$ | 222 dec. | 78 | 525 |

EXAMPLE 13

A dispersion is prepared by grinding 2 g of the dicyanomethylenepyrazolinone compound according to Example 3, 7 g of a 10% aqueous solution of polyvinyl alcohol (Polyviol V03/1040) and 4 g of water with glass beads, until a particle size of 2–4 μm is reached.

This dispersion is applied by means of a knife to a paper having a weight per unit area of 50 g/m$^2$. The amount of material applied is 4 g/m$^2$ (dry weight).

When developed by means of a precision hot press "System BASF", starting at 140°–150° C., a deep violet colour develops; contact time 80 seconds.

EXAMPLE 14

The procedure as described in Example 13 is repeated, except that the compound described in Example 13 according to Example 3 is replaced by 2 g of the dicyanomethylenepyrazolinone compound according to Example 6, to give, starting from 140°–150° C., a deep blackberry red dyeing.

What is claimed is:

1. A chromogenic dicyanomethylenepyrazolinone of the formula

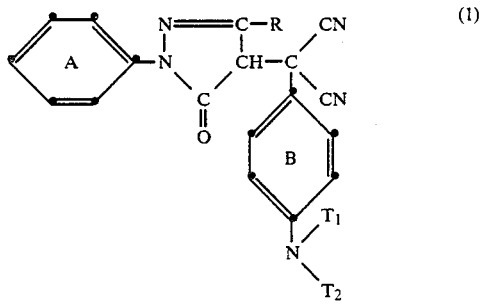
(1)

in which R is a heterocylic radical, T$_1$ and T$_2$, independently of one another, are each hydrogen, unsubstituted or halogen-, hydroxyl-, cyano- or lower alkoxy-substituted alkyl having a maximum of 12 carbon atoms, cycloalkyl having 5 to 10 carbon atoms or unsubstituted or halogen-, cyano-, lower alkyl- or lower alkoxy-(ring-)substituted phenalkyl or phenyl, or T$_1$ and T$_2$ together with the nitrogen linking them are a five- or six-membered heterocyclic radical, and rings A and B, independently of one another, are unsubstituted or substituted by halogen, cyano, nitro, lower alkyl, lower alkoxy, (lower alkyl)carbonyl or (lower alkoxy)carbonyl.

2. A dicyanomethylenepyrazolinone according to claim 1, wherein R in formula (1) is a furyl, furfuryl, thienyl, pyrrolyl, pyrazolyl, imidazolyl or pyridyl radical.

3. A dicyanomethylenepyrazolinone according to claim 1, wherein T$_1$ in formula (1) is C$_1$–C$_8$alkyl, cyclohexyl, phenyl, tolyl or benzyl and T$_2$ is hydrogen, lower alkyl or benzyl.

4. A dicyanomethylenepyrazolinone according to claim 1, wherein T$_1$ and T$_2$ in formula (1) are each lower alkyl.

5. A dicyanomethylenepyrazolinone according to claim 1, wherein benzene rings A and B in formula (1) are unsubstituted or substituted by halogen, nitro, lower alkyl or lower alkoxy.

* * * * *